United States Patent
Lam et al.

(10) Patent No.: US 11,065,296 B2
(45) Date of Patent: Jul. 20, 2021

(54) ANTIMICROBIAL PEPTIDE, ITS ANALOG AND USE

(71) Applicant: City University of Hong Kong, Kowloon (HK)

(72) Inventors: Yun Wah Lam, Kowloon (HK); Doris Wai Ting Au, Mid-Levels (HK); Hongyan Sun, Shatin (HK)

(73) Assignee: City University of Hong Kong, Kowloon (HK)

(*) Notice: Subject to any disclaimer, the term of this patent is extended or adjusted under 35 U.S.C. 154(b) by 125 days.

(21) Appl. No.: 15/927,354

(22) Filed: Mar. 21, 2018

(65) Prior Publication Data

US 2019/0374595 A1  Dec. 12, 2019

(51) Int. Cl.
| | |
|---|---|
| *A61K 38/03* | (2006.01) |
| *A61K 38/10* | (2006.01) |
| *A61K 38/16* | (2006.01) |
| *A61P 31/04* | (2006.01) |
| *C07K 14/00* | (2006.01) |
| *A61K 31/175* | (2006.01) |

(52) U.S. Cl.
CPC .............. *A61K 38/03* (2013.01); *A61P 31/04* (2018.01); *A61K 31/175* (2013.01)

(58) Field of Classification Search
CPC ........ A61K 38/03; A61K 38/10; A61K 38/16; A61K 38/1729; A61P 31/04; C07K 14/00; C07K 14/4723
USPC ...... 514/1.1, 21.5, 21.2, 21.3, 21.4, 2.3, 2.4, 514/2.7, 2.8; 530/300, 327, 324, 325, 530/326
See application file for complete search history.

(56) References Cited

U.S. PATENT DOCUMENTS 6,979,557 B2 * 12/2005 Isogai .................... C07K 14/47
435/252.3

FOREIGN PATENT DOCUMENTS

EP  1676570 A1 * 7/2006  .............. A61K 36/77

OTHER PUBLICATIONS

Q4SUM7 from UniProt, pp. 1-5. Integrated into UniProtKB/TrEMBL on Jul. 19, 2005. (Year: 2005).*

* cited by examiner

*Primary Examiner* — Julie Ha
(74) *Attorney, Agent, or Firm* — Renner Kenner Greive Bobak Taylor & Weber

(57) ABSTRACT

In various embodiments, a pharmaceutical composition comprising an effective amount of a peptide having the amino acid sequence represented by Formula (I) or an analog thereof, and a pharmaceutically tolerable excipient is described. In some embodiments, the analog of the peptide of Formula (I), comprises the peptide sequence of Formula (I) wherein one or more of the amino acids residues are modified by a) C-terminal modification; b) D-amino acid substitution; and/or c) deletion of one or more amino acid residues. A method of inhibiting the growth of a microorganism comprising contacting the microorganism in a medium with an effective amount of the peptide of Formula (I) or an analog thereof is also described, as are similar methods of treating a disease or disorder associated with microbial activity in a subject by administering an effective amount of a peptide of Formula (I) or an analog thereof and a pharmaceutically tolerable excipient to the subject.

13 Claims, 13 Drawing Sheets
Specification includes a Sequence Listing.

ANTIMICROBIAL PEPTIDE, ITS ANALOG AND USE

SEQUENCE LISTING

The Sequence Listing file entitled "mkc228sequencelisting" having a size of 3,130 bytes and a creation date of Mar. 21, 2018, that was filed with the patent application is incorporated herein by reference in its entirety.

The Sequence Listing file entitled "sequencelisting" having a size of 3,315 bytes and a creation date of Aug. 20, 2019, that was filed in the patent application is also incorporated herein by reference in its entirety.

TECHNICAL FIELD

The present application relates to a peptide and its analog, in particularly but not exclusively to an antimicrobial analog. The present invention also pertains to use of the peptide and its analog in treating a subject or inhibiting the growth of a microorganism.

BACKGROUND OF THE INVENTION

The emergence of antibiotic resistance in microorganisms is recognized as a major global threat to human health. There is therefore the dire need for new antibacterial drugs, but the number of new FDA approved antibacterial drugs have significantly fallen since the late 20th century, from 29 in the 1980s to only 9 in the 2010s. More alarmingly, as no new class of antibiotics has been discovered since 1984, all of the new antibacterial agents are derivatives of existing compounds, to which resistances are already mounting. In particular, new antibiotics against Gram-negative bacterial pathogens are desperately insufficient, largely because of their double membrane system, efficient membrane protein homeostasis and multidrug resistance efflux pump. Of the 12 bacterial families recently listed by the World Health Organization (WHO) as pathogens for which new drugs are most urgently needed, nine are gram-negative.

One of the most promising classes of natural antibacterial agents is the antimicrobial peptide (AMP). Also known as host defense peptides, AMPs play a very important role in the innate immune system. To date, more than 2000 experimentally validated AMPs have been reported, among which 70% are capable of antibacterial activity. Most AMPs are short (4-50 amino acid residues) peptides that belong to a variety of structural classes, including b-sheet, a-helical, loop, and extended peptides. Around 80% of all reported AMPs have an overall cationic charge, but with a relatively high (30%-80%) proportion of hydrophobic residues. This unique combination of biochemical properties allows them to penetrate bacterial surfaces by attaching themselves to or inserting themselves into the membrane bilayers. Other cytotoxic mechanisms of AMPs include the suppression of the biosynthesis of the bacteria cell wall and blockage of the synthesis of nucleic acids and proteins.

The past two decades can be viewed as the golden age of AMP identification, with more than 100 new AMPs discovered every year since 2000, from an exquisite list of organisms, ranging from bacteria to plants, from amphibians to reptiles. Although AMPs have been identified in circulating cells, blood plasma has rarely been used as a resource for AMP discovery: only five AMPs have been identified in plasma so far. Although the number of AMPs has been growing steadily, most of them have been discovered from terrestrial organisms, and AMPs from aquatic organisms in general have room to be explored. While the mechanism of the antibacterial effects of AMPs of some of the typical cationic amphipathic peptides has been extensively described, the molecular targets of the vast majority of AMPs remain unknown.

Accordingly, there is a strong need to provide effective antimicrobial peptides which are capable of inhibiting microbial infections, and preferably against antibiotic resistance infection.

SUMMARY OF THE INVENTION

In the first aspect, the present invention pertains to a pharmaceutical composition comprising an effective amount of a peptide or an analog thereof, and a pharmaceutically tolerable excipient, wherein the peptide comprises the amino acid sequence of SEQ ID NO: 17:
N-Terminus-Ile-Arg-Ile-Ile-Leu-Arg-Ala-Gln-Gly-Ala-Leu-Lys-Ile-C-Terminus.

In the second aspect, the present invention provides an analog of a peptide comprising the amino acid sequence of SEQ ID NO: 17,
N-Terminus-Ile-Arg-Ile-Ile-Leu-Arg-Ala-Gln-Gly-Ala-Leu-Lys-Ile-C-Terminus;
wherein one or more amino acids residues are modified by
a) C-terminal modification;
b) D-amino acid substitution; and/or
c) deletion of one or more amino acid residues.

The present invention further provides a method of inhibiting the growth of a microorganism, comprising contacting the microorganism in a medium with an effective amount of a peptide or an analog thereof, wherein the peptide comprises the amino acid sequence of SEQ ID NO: 17 as described above.

Still further, the present invention pertains to a method of treating a disease or disorder associated with microbial activity in a subject, comprising administering an effective amount of a peptide or an analog thereof to the subject, wherein the peptide comprises the amino acid sequence of SEQ ID NO: 17 as described above.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF THE EMBODIMENTS

Figure 1:
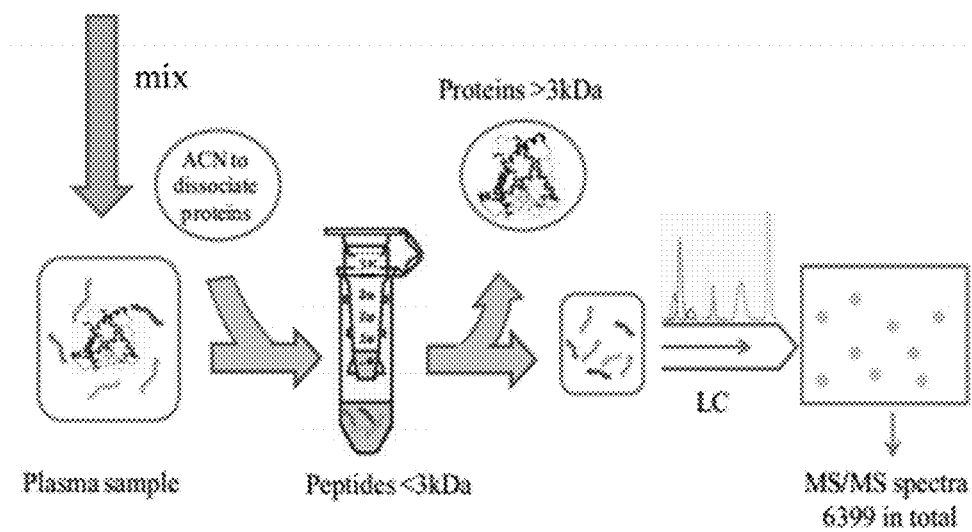
FIG. 1 is a schematic diagram showing identification and characterization of small circulating peptides (SCPs) in medaka plasma.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents.

"Consisting of" means that the material solely consists of, i.e. is formed by the respective element. As used herein, the forms "a," "an," and "the," are intended to include the singular and plural forms unless the context clearly indicates otherwise.

Other than in the working examples, or where otherwise indicated, all numbers used herein should be understood as modified in all instances by the term "about" The term "about" when used in connection with a number can mean, for example, ±2%.

The present invention in the first aspect provides a peptide and an analog thereof in particular an antimicrobial peptide isolated from plasma of a fish and an analog thereof. The fish is preferably a species of genus Oryzias. In an embodiment, the peptide is isolated from O. latipes which is also known as Japanese rice fish or medaka. The term "antimicrobial peptide" as used herein refers to a peptide which is capable of inhibiting the growth or killing a microorganism in particular pathogenic microorganism. The peptide of the present invention may be isolated or derived from living naturally occurring molecules or synthesized from any peptide production methods, according to the description provided herein. Preferably, the peptide comprises 4 to 50 amino acid residues, 5 to 30 amino acid residues, 8 to 20 amino acid residues, or preferably 10 to 15 amino acid residues.

In an embodiment, the peptide of the present invention is isolated from O. latipes and comprises 13 amino acid residues. In particular, the peptide comprises an amino acid sequence of SEQ ID NO: 17:

N-Terminus-Ile-Arg-Ile-Ile-Leu-Arg-Ala-Gln-Gly-Ala-Leu-Lys-Ile-C-Terminus.

Without wishing to be bound by theory, this peptide is capable of inhibiting the growth of a microorganism such as a bacterium in particular a pathogenic bacterium. This peptide can suppress the CpxR expression and/or induce RpoE expression, which will be described in detail.

The term "analog" refers to a structural derivate of a corresponding peptide that differs from it by at least one element. The "analog" of the present invention particularly refers to a derivate having at least one identical bioactivity as that of the corresponding peptide. Preferably, an analog of the peptide comprising the amino acid sequence of SEQ ID NO: 17 has one or more amino acid residues modified by:
 a) C-terminal modification, such as but not limiting to methylation, amidation, reduction, or esterification, preferably amidation;
 b) D-amino acid substitution; and/or
 c) deletion of one or more amino acid residues.

In an embodiment, the analog comprises a C-terminal amidiated peptide.

In another embodiment, the analog comprises or substantially consists of D-amino acids. In other words, the analog may be a D-isomer of the of SEQ ID NO: 17 by partial or complete substitution of D-amino acids.

Alternatively, the analog may comprise a shortened amino acid sequence as compared to the corresponding peptide, i.e. the peptide of SEQ ID NO: 17. In particular, the analog may comprise 5-10 amino acid residues derived from the peptide.

An ordinary person having skills in the art would be capable of synthesizing the peptide and its analog of the present invention according to the disclosure herein. For example, the peptide may be obtained from a fish infected by a bacterium. A person skilled in the art would appreciate suitable methods extracting, purifying and isolating the peptide and synthesizing the corresponding analog.

In an embodiment, the peptide or the analog has a net charge of at least 5, preferably at least 8. In particular, the peptide or the analog has a hydrophobic ratio of more than 30%.

In another aspect, the present invention provides a pharmaceutical composition comprising an effective amount of a peptide or an analog thereof, and a pharmaceutically acceptable carrier, wherein the peptide comprises the amino acid sequence of SEQ ID NO: 17:
 N-Terminus-Ile-Arg-Ile-Ile-Leu-Arg-Ala-Gln-Gly-Ala-Leu-Lys-Ile-C-Terminus.

The peptide and its analog are as defined above. Preferably, the analog comprises one or more amino acids residues modified by
 a) C-terminal modification, in particular C-terminal amidation;
 b) D-amino acid substitution, so as to forming a D-isomer of the peptide; and/or
 c) deletion of one or more amino acid residues.

Preferably, the peptide or the analog has a concentration of about 0.1 µM to about 150 µM, or 1 µM to about 140 µM, in the pharmaceutical composition.

The peptide and/or the analog of the present invention may be administered in form of a pharmaceutical composition comprising said peptide and/or analog and a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof. A person of skill in the art is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition can be present in solid, semisolid or liquid form to be administered by an oral or parenteral route to the subject.

In an embodiment, the peptide and/or analog of the present invention can be used as a single compound for treating a subject in particular with a disease or disorder associated with microbial activity.

In other embodiments, the peptide and/or analog of the present invention is administered in combination with other therapeutically effective treatments such as other compounds used for treating microbial infection.

The expression "effective amount" and "effective dose" generally denote an amount sufficient to produce therapeutically desirable results, wherein the exact nature of the result varies depending on the specific disorder which is treated. When the disorder is a bacterial infection, the result may be a reduction of the inflammation such as a reduction of inflammatory markers, a reduction of the growth of the bacterium, or alleviation of the associated symptoms.

The effective amount of the peptide and/or analog of the present invention may depend on the species, body weight, age and individual conditions of the subject and can be determined by standard procedures such as with cell cultures or experimental animals.

The term "subject" used herein refers to a living organism and can include but is not limited to a mammal and a fish. The subject may be a mammal, preferably a human. The subject may be a fish. In an embodiment, the subject may be suffering from an antibiotic-resistant bacterial infection, i.e. the subject is infected by a bacterium resistant to a certain antibiotic. The peptide and/or analog of the present invention is found to be useful against antibiotic-resistance bacterial infection, and in particular suppress periplasmic protein folding.

Accordingly, the present invention also provides a method of treating a disease or disorder associated with microbial activity in a subject as described above, comprising administering an effective amount of a peptide or an analog thereof as described above to the subject, wherein the peptide comprises the amino acid sequence of SEQ ID NO: 17:
 N-Terminus-Ile-Arg-Ile-Ile-Leu-Arg-Ala-Gln-Gly-Ala-Leu-Lys-Ile-C-Terminus.

Preferably, the disease or disorder is associated with a bacterial infection. In particular, the bacterial infection is caused by a bacterium of a species of genus selected from *Enterococcus, Streptococcaceae, Aeromonas, Vibrio, Escherichia, Staphylococcus, Edwardsiella*, or *Acinetobacter*. In an embodiment, the bacterial infection is caused by a gram-negative bacterium selected from *A. hydrophila, V. alginolyticus, E. coli, E. tarda, A. baumannii* or a combination thereof. In another embodiment, the bacterial infection is caused by a gram-positive bacterium selected from *S. faecalis, S. pyogenes, S. aureus*, or a combination thereof.

In a particular embodiment, the subject suffers from an antibiotic-resistant bacterial infection. The antibiotic may be ampicillin, beta-lactam or the like.

The subject is preferably administered with the peptide or analog at a concentration of about 0.1 µM to about 150 µM, or about 1 µM to about 140 µM. As described earlier, the effective amount of the peptide and/or analog of the present invention may depend on the species, body weight, age and individual conditions of the subject and can be determined by standard procedures such as with cell cultures or experimental animals.

Still further, the present invention also pertains to a method of inhibiting the growth of a microorganism, comprising contacting the microorganism as described above in a medium with an effective amount of a peptide or an analog thereof as described above, wherein the peptide comprises the amino acid sequence of SEQ ID NO: 17:

N-Terminus-Ile-Arg-Ile-Ile-Leu-Arg-Ala-Gln-Gly-Ala-Leu-Lys-Ile-C-Terminus.

Preferably, the microorganism is a bacterium in particular of a species of genus selected from *Enterococcus, Streptococcaceae, Aeromonas, Vibrio, Escherichia, Staphylococcus, Edwardsiella,* or *Acinetobacter*. The bacterium may be a gram-negative bacterium or gram-positive bacterium as defined above.

The method further comprises a step of incubating the microorganism with the peptide or analog thereof for at least 1 h, at least 3 h, or at least 5 h. In an embodiment, the microorganism is incubated with the peptide and/or analog overnight.

The examples set out below further illustrate the invention. The preferred embodiments described above and the drawings as well as examples given below represent preferred or exemplary embodiments and a skilled person will understand that the reference to those embodiments or examples is not intended to be limiting.

EXAMPLES

Example 1

Preparing Peptides from *O. laptipes*

The inventors established a database of naturally occurring peptides in the plasma of Japanese medaka. This was achieved by subjecting short peptides isolated from medaka plasma to a mass spectrometric analysis (as shown in FIG. 1). The inventors envisaged that the composition of the circulating peptides is highly dynamic, and subject to conditions such as sex, age and health status. As shown in Table 1, to avoid bias due to the predominant expression of peptides in any specific condition, the plasma collected from fishes of both sexes and different ages were pooled together. Bacterially infected fish were also included in the supermix to allow for the detection of potential infection-associated peptides. The inventors then focused on relatively short peptides in particular peptides having a size less than 3 kD.

TABLE 1

Fishes used in preparing the peptides

| | Healthy | | 3 day post infection | |
|---|---|---|---|---|
| Fish age | Female | Male | Female | Male |
| 4 months | 2 | 2 | 2 | 2 |
| 8 months | 1 | 1 | 1 | 1 |
| 11 months | 1 | 1 | 1 | 1 |
| 14 months | 1 | 1 | 1 | 1 |
| 15 months | 1 | 1 | 1 | 1 |
| 19 months | 1 | 1 | 1 | 1 |
| 22 months | 1 | 1 | 1 | 1 |

Figure 2A:
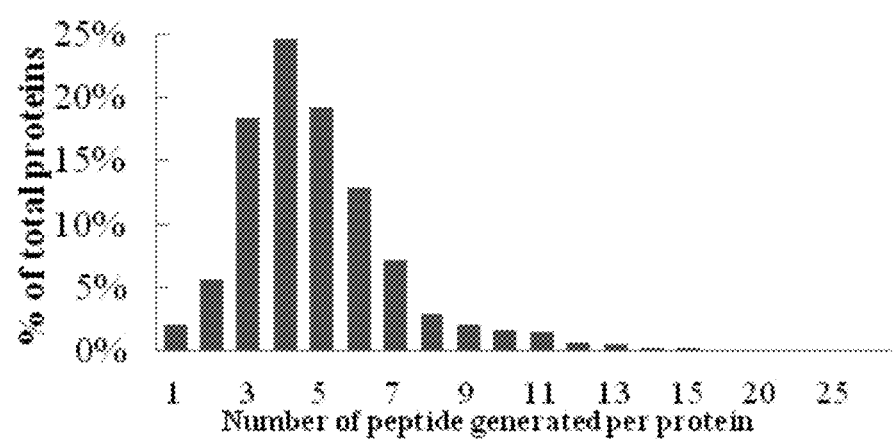
FIG. 2A is a plot showing the distribution of parent proteins of the identified SCPs.
Figure 2B:
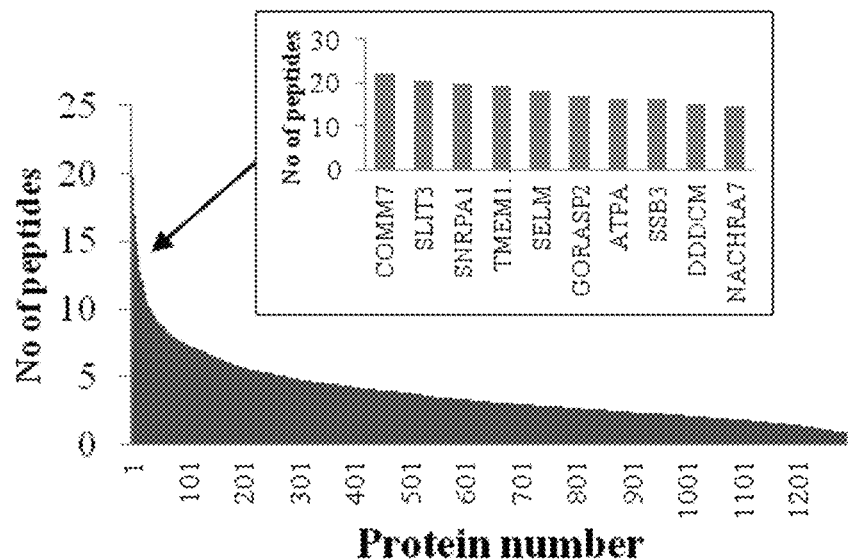
FIG. 2B is a plot showing the identity of parent proteins that give rise to the most number of SCPs.
Figure 2C:
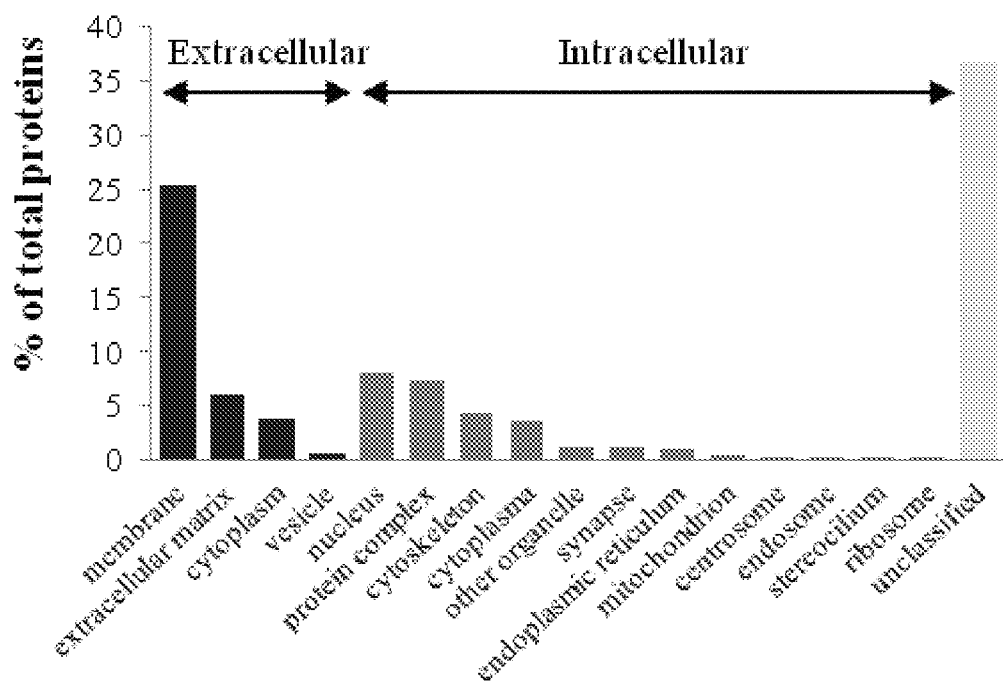
FIGS. 2C and 2D show the results obtained from gene ontology analysis of parent proteins in terms of biological processes and cellular components.
Figure 2D:
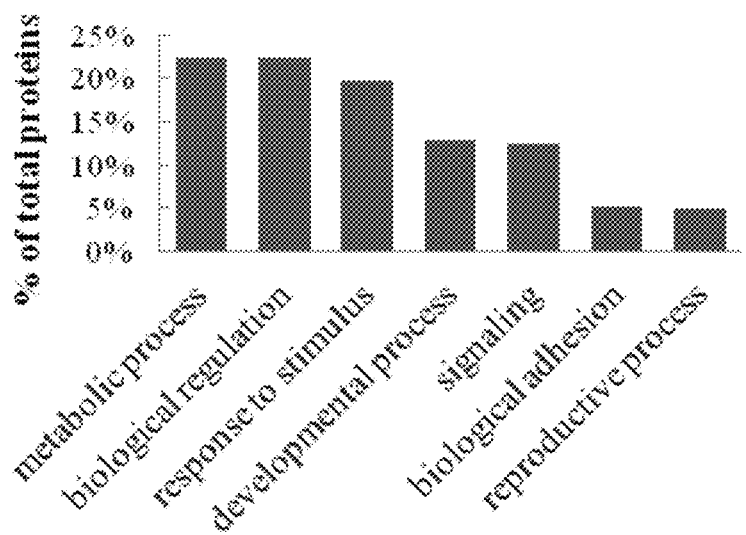
Figure 2E:
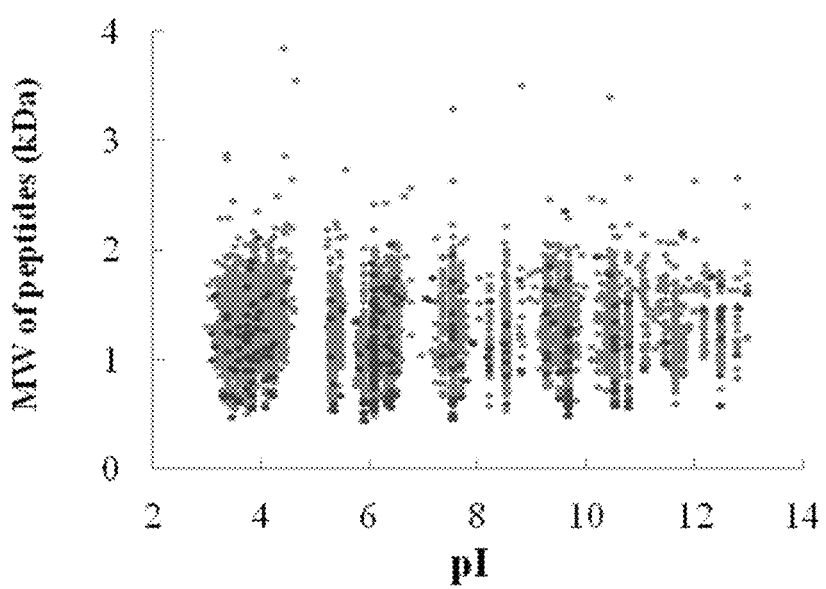
FIG. 2E is a plot showing the distribution of molecular weight and isoelectric points of all SCPs identified (black dots). Grey dots represent SCPs that are homologous to existing AMPs.
Figure 2F:
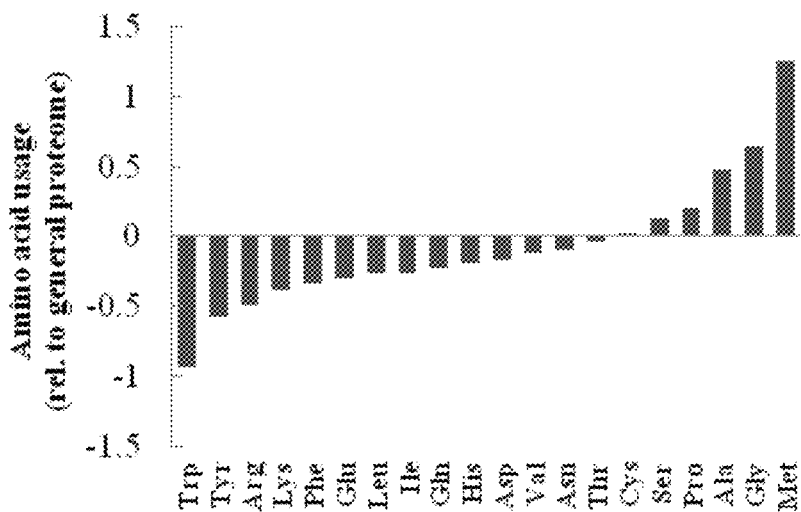
FIG. 2F is a plot showing the amino acid usage of identified SCPs, relative to amino acid usage of general medaka proteome.

With this approach, 6,480 unique peptide sequences were identified, in which 81 are peptides with overlapping sequences. The inventors eliminated all redundancy from the raw dataset, which resulted in an inventory of 6399 short circulating peptides (SCPs) in the medaka. These SCPs can be mapped to 1289 proteins. More than 60% of the parent proteins produce 3-5 peptides, with a small number of proteins giving rise to over 20 peptides (FIG. 2A). The parent proteins that generate the most SCPs, such as COMM domain-containing protein 7-like (COMM7) and uncharacterized protein (SLIT3), are not abundant serum proteins (FIG. 2B). 23% of these parent proteins have intracellular origins (FIGS. 2C-D), which suggests that the genesis of SCPs is not a result of the nonspecific degradation of extracellular proteins. The inventors analyzed the physiochemical properties of the detected SCPs. More than 99% of the SCPs are less than 3 kD. It is observed that there is a slight bias towards acidic peptides within the SCPs (FIG. 2E). The amino acid usage of the SCPs, when compared to that of the general medaka proteome, revealed a preference towards nonpolar amino acids such as methionine, glycine and alanine, while aromatic amino acids are underrepresented (FIG. 2F).

A comparison of the sequences between the collection of SCPs and the 2767 experimentally validated AMPs in the CAMP database (CAMP$_{R3}$) revealed that 301 of the SCPs are highly homologous to known AMPs, of which 17 have previously been reported in other fish species.

Figure 3:
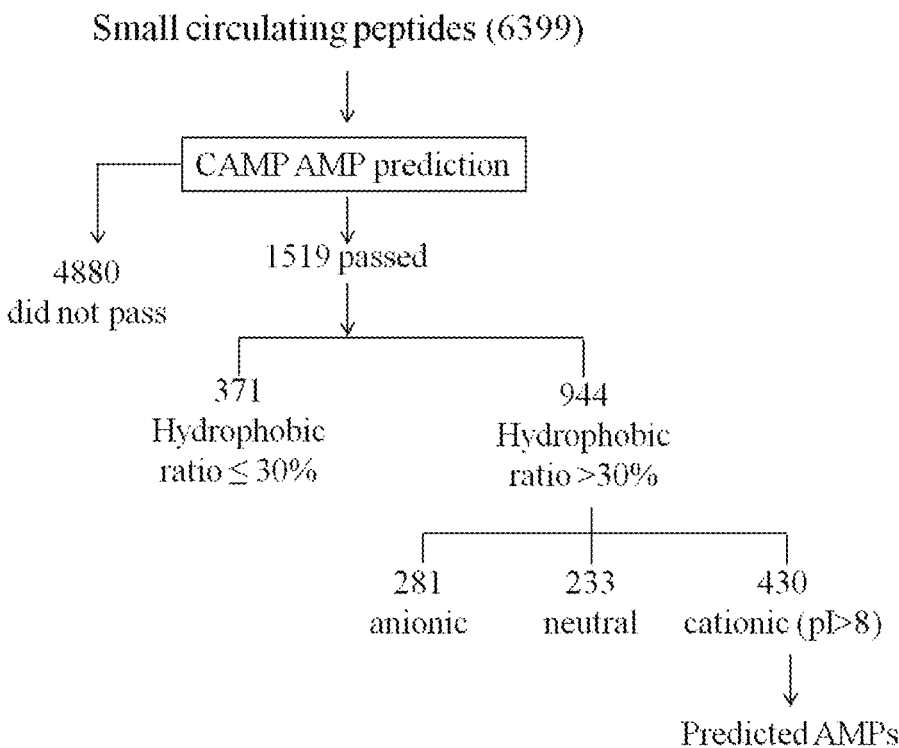
FIG. 3 is a diagram showing how the identified SCPs are screened by prediction algorithms for AMPs from $CAMP_{R3}$ database. Those with high scores further selected for their charge and hydrophobicity.

Of the remaining SCPs, 1519 (24%) satisfy the CAMP prediction algorithm for AMPs as potential AMPs (FIG. 3). In order to increase the accuracy of prediction, the inventors further limited the shortlisted AMPs to amphipathic and cationic peptides, since they account for the majority of currently known AMPs. There are 430 peptides from the SCP database that satisfied these criteria. To assess the accuracy of the AMP prediction, the inventors synthesized 53 of the shortlisted SCPs and tested their toxicity against both Gram positive (*S. aureus*) and negative (*E. coli*) bacteria. Eight of these peptides (15%) demonstrated significant antimicrobial activity. The inventors also synthesized a number of non-cationic peptides from the CAMP-predicted set as the controls, as well as a subset of peptides that did not satisfy the CAMP prediction algorithm (FIG. 3). None of these peptides exhibited any antibacterial effects.

Figure 4:
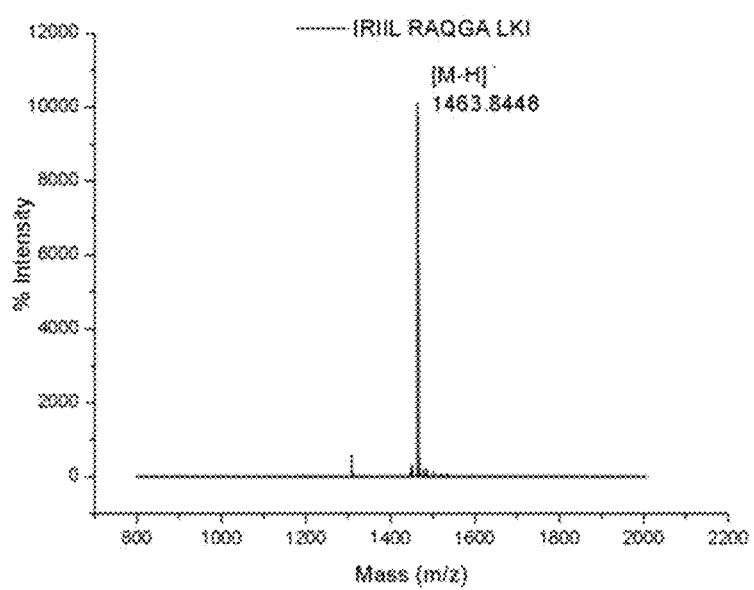
FIG. 4 is a mass spectrum obtained from MALDI-TOF MS analysis of Peptide A prepared from Japanese medaka.

One of the tested SCPs a 13-mer peptide (IRIIL-RAQGALKI, also denoted as Peptide A) that is derived from vacuolar protein sorting-associated protein 13D-like (Vps13D), which demonstrated toxicity against both Gram positive and negative bacteria. This peptide was therefore subjected to further characterization. The purity of this peptide is shown in FIGS. 4A and 4B.

Example 2

Antibacterial Activity of Peptide

Figure 5A:
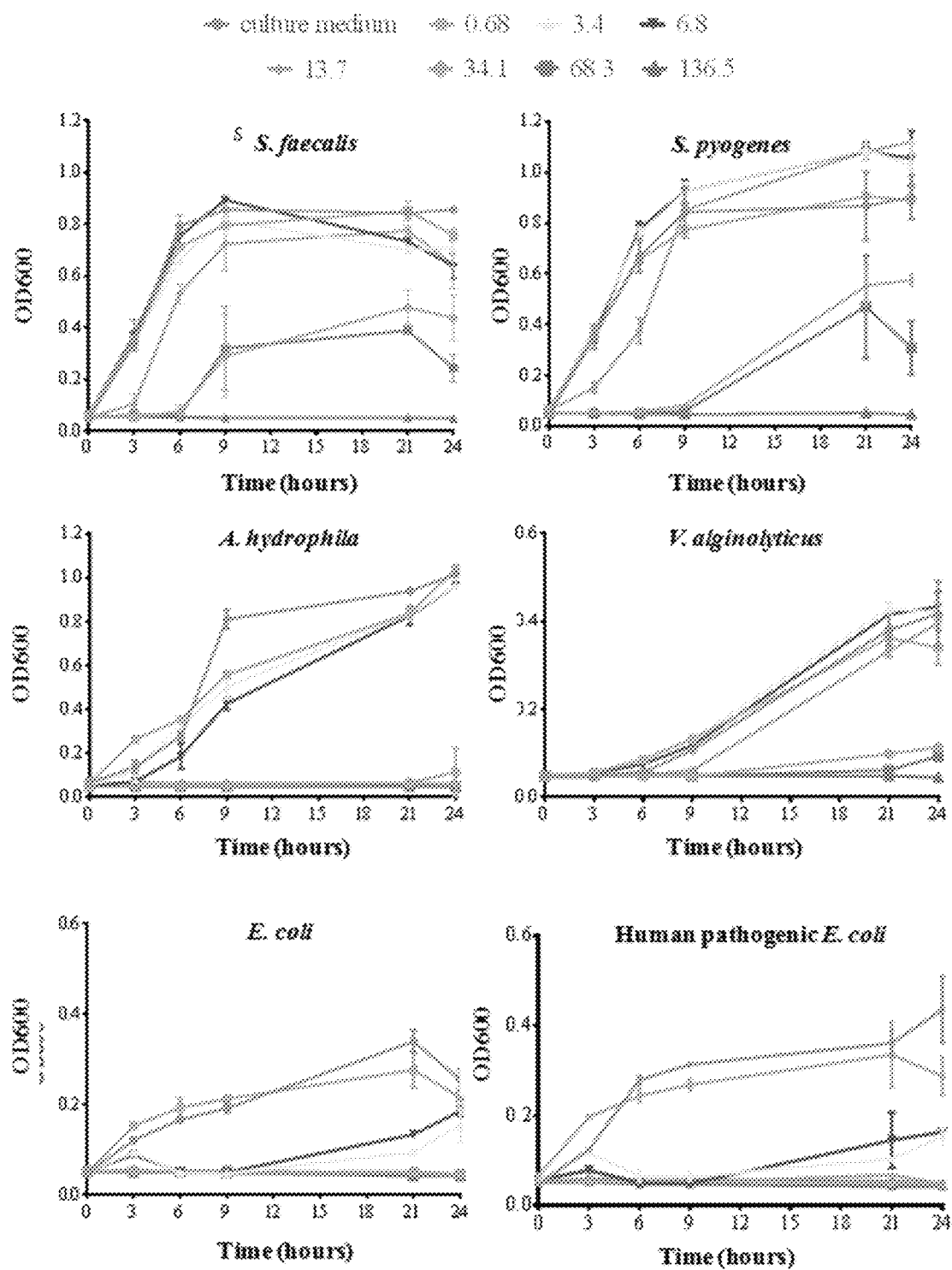
FIGS. 5A and 5B show the antibacterial effect of Peptide A whose sequence is shown as SEQ ID NO: 17 on various bacteria, i.e. S. faecalis, S. pyogenes, S. aureus, A. hydrophila, V. alginolyticus, E. coli, E. tarda, and A. baumannii. Unit of peptide concentration: µM. The experiments were repeated three times. Results are OD600 values of different groups. Results are expressed as mean±SD, n=3.
Figure 5B:
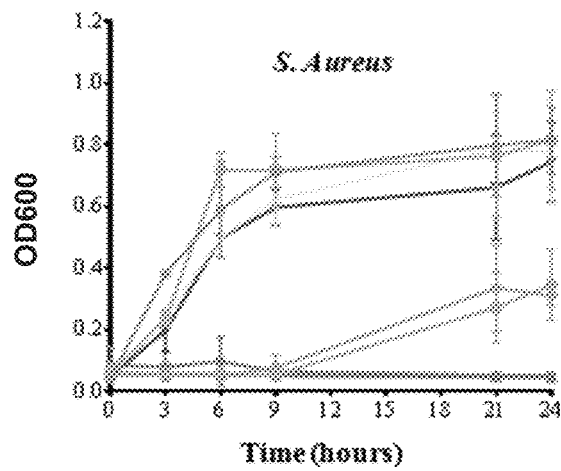
Figure 5B:
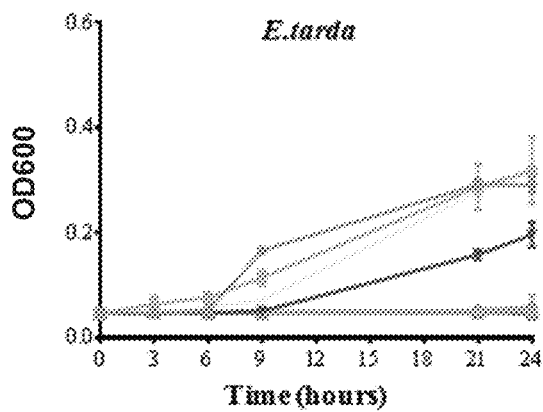
Figure 5B:
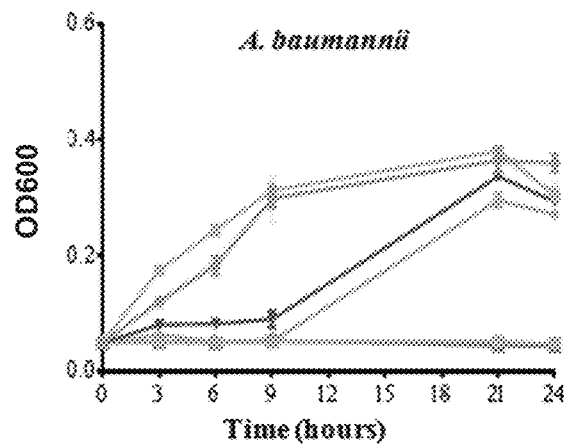

The newly identified AMP suppresses envelope stress responses in Gram-negative bacteria. The antibacterial activity of the Peptide A against a panel of Gram-positive and Gram-negative bacteria (FIG. 5A, 5B and Table 2) was determined. This peptide showed a broad bactericidal effect, with MIC ranging from 3.4 to 34.1 μM. Significantly, this peptide was also found effective on a number of antibiotic resistant strains, including beta-lactam resistant bacteria (Table 2).

TABLE 2

Antibacterial activity of identified peptides on
normal (upper) or drug resistant bacteria (lower)

| Bacteria | Gram (+/−) | MICs (μM) |
|---|---|---|
| Streptococcus Faecalis | + | 34.1 |
| Streptococcus pyogenes ATCC 14289 | + | 34.1 |
| Staphylococcus aureus ATCC 6538 | + | 13.7 |
| Bacillus subtilis 168 | + | 10.9 |
| Staphylococcus aureus ATCC 29213 | + | 64 |
| Aeromonas hydrophila ATCC 49140 | − | 13.7 |
| Vibrio alginolyticus ATCC 33840 | − | 34.1 |
| Edwardsiella tarda PE210 | − | 6.8 |
| E. cloacae BAA-1143 | − | 21.8 |
| Acinetobacter baumannii ATCC 19606 | − | 6.8 |
| Escherichia coli ATCC 10536 | − | 3.4 |
| Escherichia coli (pathogenic) | − | 3.4 |
| Escherichia coli BL21 (DE3) | − | 5.5 |
| Klebsiella pneumoniae (NDM-1) ATCC BAA-2470 | − | 21.8 |
| Escherichia coli (NDM-1) ATCC BAA-2469 | − | 10.9 |
| NDM-1/BL21 (DE3) | − | 2.7 |
| SHV-1/BL21 (DE3) | − | 2.7 |
| TEM-1/BL21 (DE3) | − | 5.5 |
| MCR-1/BL21 (DE3) | − | 10.9 |
| Methicillin-resistant S. aureus ATCC BAA-41 | + | 21.8 |
| Multidrug-resistant S. aureus ATCC BAA-44 | + | 21.8 |
| Staphylococcus epidermidis ATCC 12228 | + | 2.7 |
| Pseudomonas aeruginosa A | − | 34.1 |

MIC denotes the lowest concentration of an antimicrobial agent that can inhibit the growth of bacteria after overnight incubation.

Figure 6:
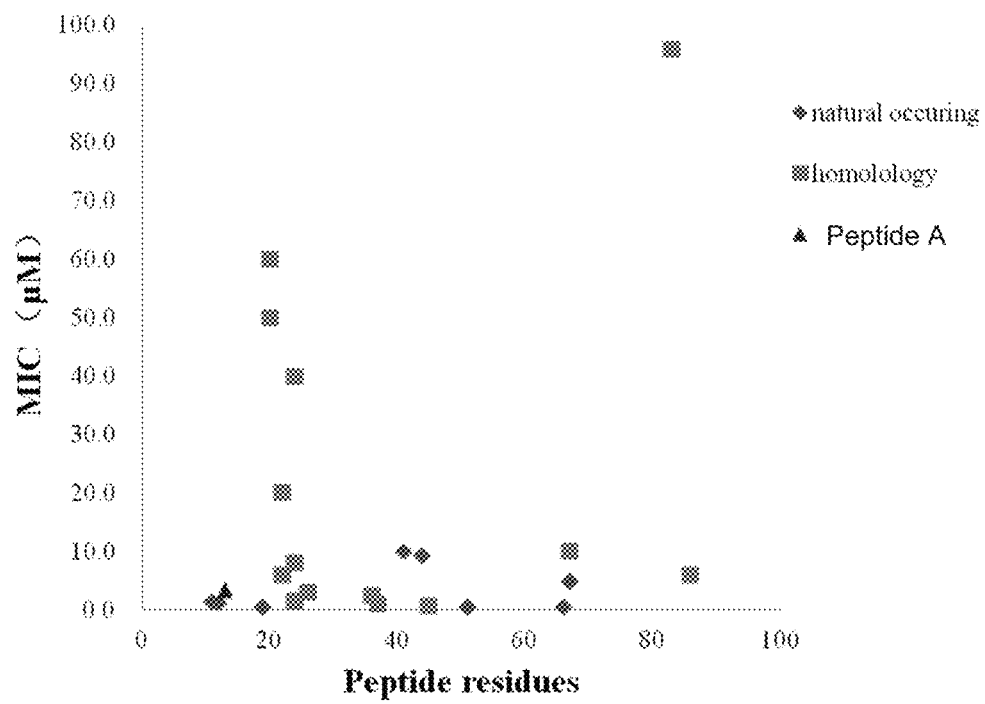
FIG. 6 is a plot showing the minimum inhibitory concentration (MIC) of antimicrobial peptides (AMPs) isolated from fish tissues having different peptide length. The diamonds represent AMPs isolated from fish tissues, the rectangles represent AMPs synthesized based on sequence homology with other AMPs, while the triangle represents Peptide A.
Figure 7A:
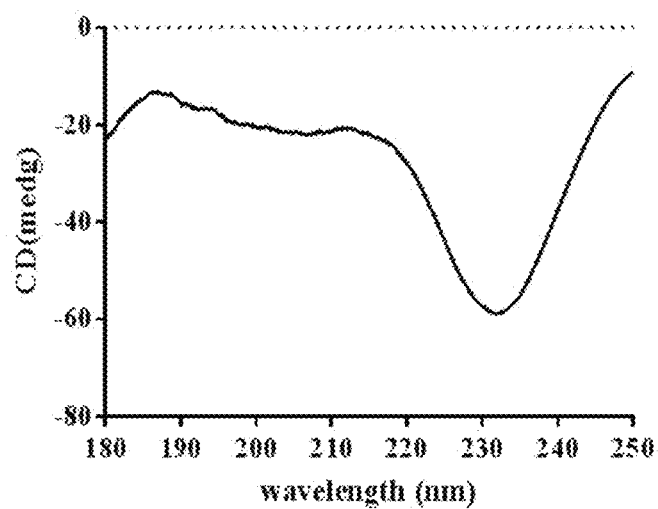
FIG. 7A is a circular dichroism (CD) spectroscopy of AMPs including Peptide A in distilled water.
Figure 7B:
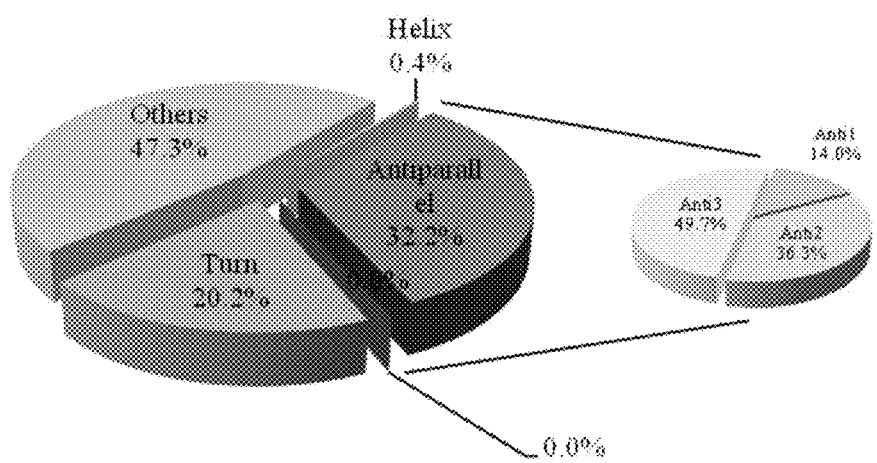
FIG. 7B is a diagram showing an estimation of secondary structure prepared by using BeStSel (http://bestsel.elte.hu/). BeStSel distinguished parallel and antiparallel β-sheets and divided antiparallel β-sheets into three subgroups: left-hand twisted (anti1), relaxed (anti2), and right-hand twisted (anti3).

The inventors surveyed the MIC of 22 known antibacterial AMPs in fish, and observed that this peptide is among the shortest and most potent (see FIG. 6). CD spectroscopy of the synthetic peptide (see FIGS. 7A and 7B) suggested that this AMP adopts a secondary structure of right-hand twisted (anti3) beta sheet, a configuration commonly found in other AMPs.

Figure 8A:
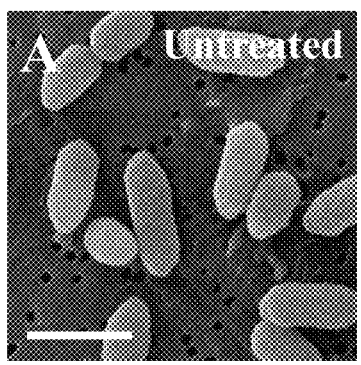
FIG. 8A shows the scanning electron micrograph of E. tarda without treatment of Peptide A.
Figure 8B:
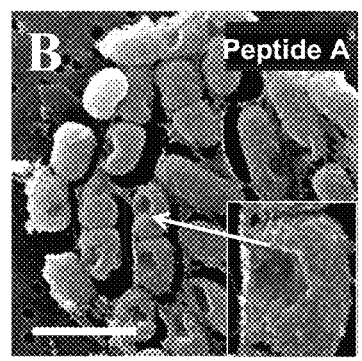
FIG. 8B shows the scanning electron micrograph of E. tarda with the treatment of Peptide A (34.1 µM) for 30 min.
Figure 8C:
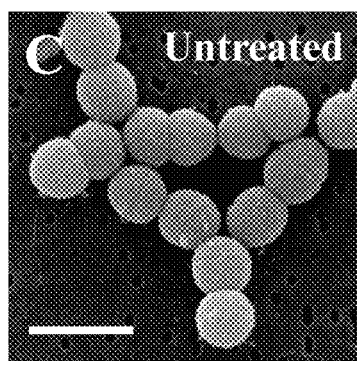
FIG. 8C shows the scanning electron micrograph of S. pyogenes without treatment of Peptide A.
Figure 8D:
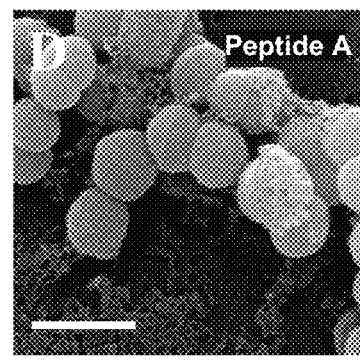
FIG. 8D shows the scanning electron micrograph of S. pyogenes with the treatment of Peptide A (34.1 µM) for 30 min. Bars=2 µm. Representative images from four replicates.
Figure 9A:
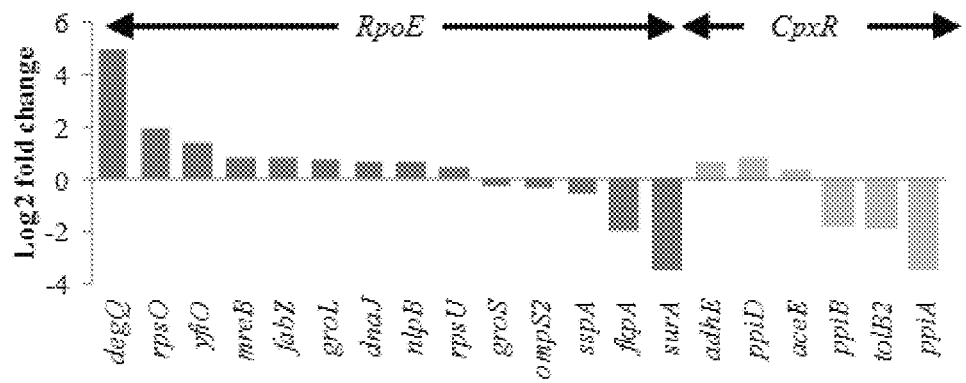
FIG. 9A is a plot showing the average of fold change of selected E. tarda proteins after 60 min of Peptide A treatment at 6.8 µM. Results represented as average of log 2 relative fold change (treatment/control).

The scanning electron microscopy (SEM) analysis indicated that this peptide (at 34.1 μM) causes cell morphology changes in both E. tarda (FIGS. 8A and 8B) and S. pyogenes (FIGS. 8C and 8D) within 30 min of treatment. Interestingly, it appeared to cause more severe morphology changes on E. tarda (FIG. 8B) than on S. pyogenes (FIG. 8C), consistent with its higher potency against Gram-negative bacteria. To delineate its bactericidal mechanism on Gram-negative bacteria, the inventors conducted a quantitative proteomic analysis on E. tarda treated with the peptide at 6.8 μM for 1 hr. A total of 770 proteins were identified among three technical repeats among which 251 proteins were of high confidence (identification in two out of three repeats and supported by more than one peptide). 74 of these proteins were found differentially expressed (at least one-fold difference) in response to the AMP. The proteins involved in outer membrane assembly, peptidoglycan synthesis, and metal ion binding were induced, possibly constituting a cellular defense against the AMP toxicity. Interestingly, members of the Peptidyl-prolyl isomerase (PPlases) family, including PpiA, PpiB, FkpA and SurA, were highly suppressed (FIG. 9A). These proteins were all involved in the periplasmic stress responses in Gram-negative bacteria. This suggests the AMP may induce an inhibition of protein folding homeostasis. This AMP which is denoted as Peptide A is considered as a blocker of INter-membrane stress responses of Gram-negative bacteria.

Example 3

Peptide A Suppresses Bacterial CpxR and Induce RpoE Signaling Pathway

Figure 9B:
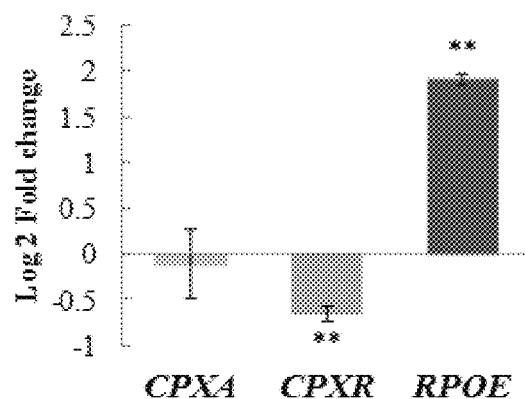
FIG. 9B is a plot showing the relative expression levels of CpxA, CpxR and RpoE in E. tarda upon treatment with Peptide A for 60 min at 6.8 µM. Results are expressed as 2^(−Delta Delta C (T)).

The periplasmic stress responses in bacteria are regulated by RpoE signaling and the CPX two component pathway. The inventors characterized the mRNA levels of CpxR and RpoE in E. tarda treated with the Peptide A at 6.8 μM for 1 hr. As shown in FIG. 9B, the expression of CpxR, one of the components in the CPX two-component system, is significantly reduced after treatment with the Peptide A.

Figure 9C:
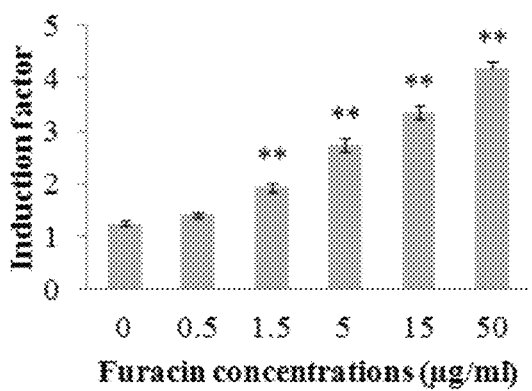
FIG. 9C is a plot showing the CpxR gene expression in E. tarda after treatment with Peptide A (6.8 µM), Piscidin (7.5 µM), Ampicillin (143 µM) and Peptide A+Ampicillin (3.4 µM; 71.5 µM) for 1 hour. Results are expressed as 2^(−Delta Delta C (T)). Each bar represents mean (n=3) with error bars indicating SD.  represents P<0.05, comparison with untreated bacteria group. Results expressed as log 2 fold change normalized with control group.

CpxA, the other component of this system, remains unaffected by the Peptide A. The inhibition of CpxR can also be found in E. coli (FIG. 9B). Interestingly, the expression of RpoE was significantly induced by the Peptide A. This is consistent with the up-regulation of DegQ, RpsO and YfiO, which are the downstream proteins of the RpoE pathway, as shown in the proteomic data (FIG. 9A). These results indicate that the Peptide A can selectively suppress the CPX pathway by inhibiting the expression of CpxR. The inhibition of the expression of CpxR and periplasmic stress responses by an AMP has not been reported before. Another fish AMP (Piscidin) or antibiotic (Ampicillin) has been found to have no effect on the level of expression of CpxR (FIG. 9C), thus suggesting that the Peptide A represents a new class of AMPs that target CPX two component pathways in bacteria. Ampicillin significantly induced the expression level of CpxR, consistent with the reported effect of antibiotics on CpxR and on envelope stress response. Notably, the Peptide A could revert the induction of CpxR expression by ampicillin (FIG. 9C). Accordingly, the Peptide A may be used in treatment of suppressing CpxR-mediated antibiotic resistance.

Figure 9D:
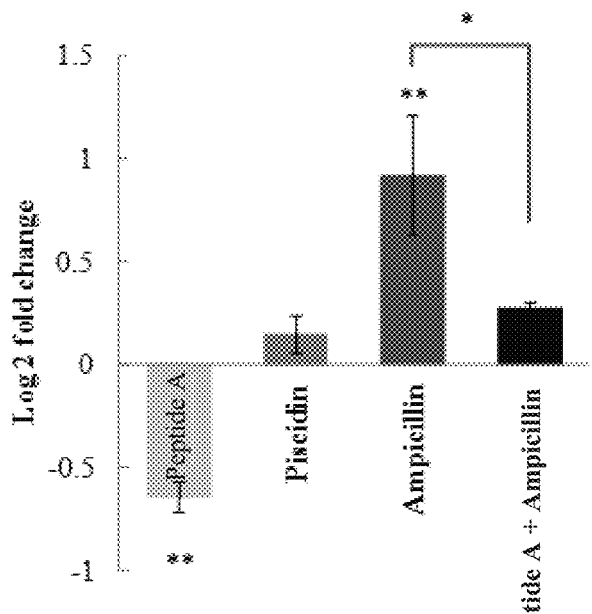
FIG. 9D is a plot showing the SOS response of E. coli treated with different doses of Furacin.
Figure 9E:
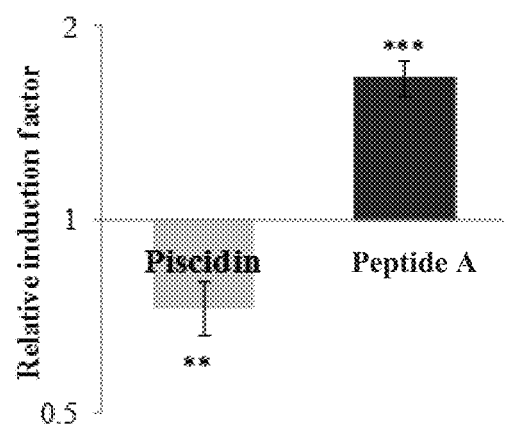
FIG. 9E is a plot showing the SOS response of E. coli treated with Piscidin (3.77 µM), Peptide A (3.4 µM) for 120 min. Concentrations used represent MIC of respective compounds for E. coli. Result shown as induction factor (IF: B-galactosidase/alkaline phosphatase) and normalized with culture medium group. Statistically significant difference as compared to culture medium controls (: p<0.01, n=3).

Without wishing to be limited by theory, it is believed that the Peptide A suppresses the ability of bacteria to alleviate membrane protein misfolding and leads to envelope stresses. As the induction of envelope stresses in Gram-negative bacteria generally leads to DNA damage, the inventors investigated whether the treatment with the Peptide A can induce an SOS response in E. coli. As a positive control (FIG. 9D), Furacin, an antibiotic known to trigger SOS responses, can induce the dose-dependent expression of LacZ in the chromotest. As shown in FIG. 9E, the data indicate that treatment with the Peptide A leads to a consistent induction of SOS response. Interestingly, another fish AMP, Piscidin, shows no effect on SOS response.

Figure 10:
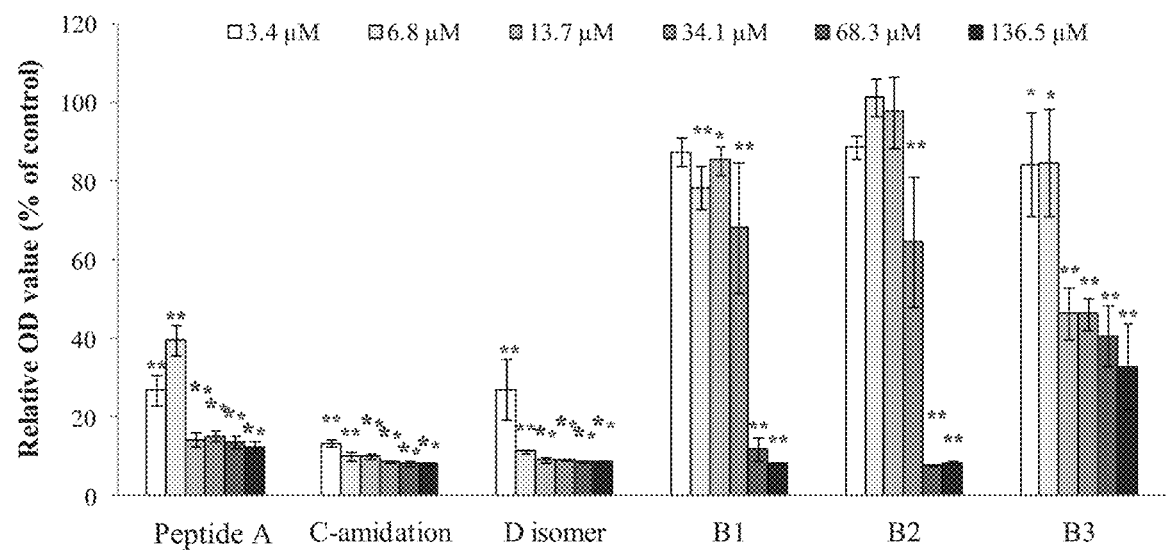
FIG. 10 is a plot showing the antibacterial activities of the peptide analogs on E. coli. C-amidation: C-terminus amidated Peptide A; B1: RIILRAQGALKI; B2: IRIIL-RAQGALK; B3: RIILR. Results expressed as relative OD600 compared to culture medium group (%) (*: p<0.05, **: p<0.01, n=3)

Antibacterial activity of the Peptide A may be dependent on its sequence. It is found that chemical modifications of the Peptide A, such as by C-terminus amidation and complete D-amino acid substitution, slightly increased the antibacterial activity of the Peptide A (FIG. 10), consistent with their role in enhancing peptide stability. However, the removal of a single amino acid, either from the C- or N-terminus, could reduce the antibacterial effect of Peptide A (as represented by peptides B1 and B2 in FIG. 10). As the two terminal residues of the Peptide A do not contribute to the net charge and hydrophobicity of this peptide, it is believed that the bactericidal effect of Peptide A depends on its secondary structure rather than chemical properties. A 5-residue peptide that contains the cationic portion of Peptide A (represented by peptide B in FIG. 10) showed much weaker antibacterial activity than full-length Peptide A.

Example 4

Cytotoxic Effect of Peptide A in Mammalian Cells and Fish

Figure 11A:
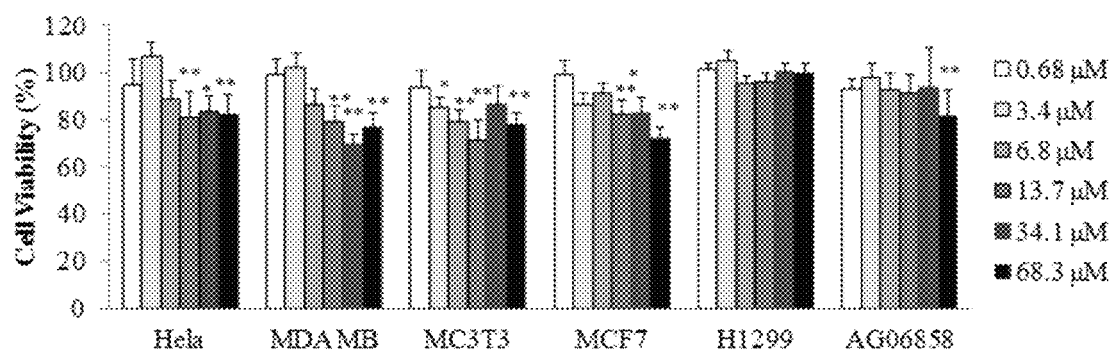
FIG. 11A is a plot showing the effect of Peptide A on viability of cultured mammalian cells, incubated for 48 h in the presence of Peptide A at different concentrations (µg/ml), as determined by MTT assay. Cell viability represented as peptide treated cell numbers over medium-only control. Statistically significant difference as compared to controls (*: p<0.05, : p<0.01, n=4).
Figure 11B:
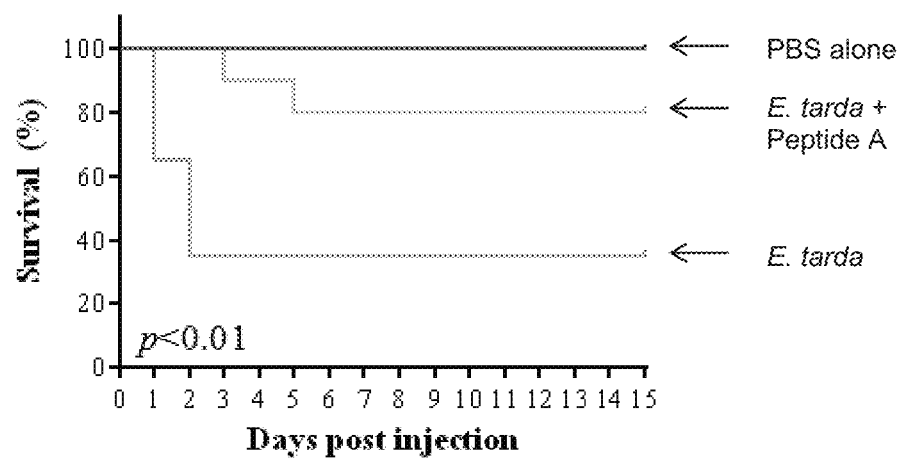
FIG. 11B is a plot showing the ability of Peptide A to protect medaka from lethal challenge of E. tarda ($10^4$ CFU/fish). Medaka was injected with 1 µl of Peptide A (0.68 mM), with 1 µl of E. tarda ($10^7$ CFU/ml) and Peptide A (0.68 mM) mixture, or with E. tarda alone (1 µl of E. tarda:$10^7$ CFU/ml).

The cytotoxic effects of Peptide A were tested against six mammalian cell lines (HeLa, MDA-MB, MC3T3, MCF7, H1299, and AG06858) (FIG. 11A). No obvious toxicity was detected at concentrations close to the MIC for gram-negative bacteria. Finally, no adverse effect was observed in adult Medaka fish intraperitoneally injected with 1 µg of the peptide for up to 14 days (FIG. 11B). Taken together, Peptide A is nontoxic to fish and mammalian cells at its bactericidal concentrations, and therefore can be applied in antimicrobial applications.

Figure 11C:
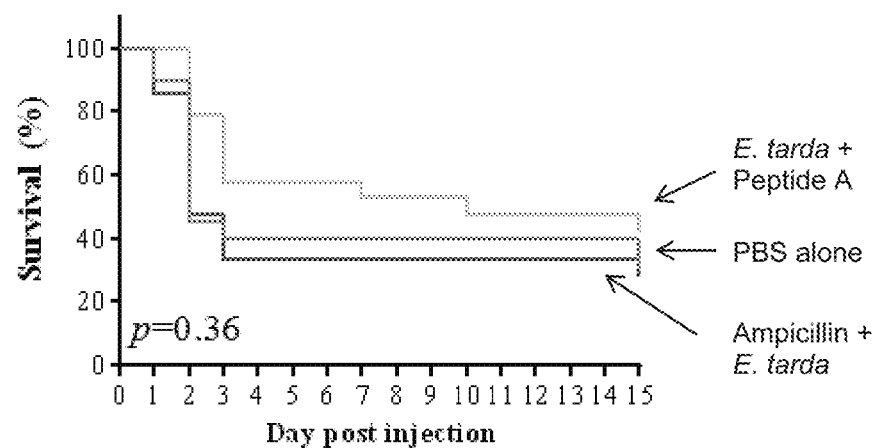
FIG. 11C is a plot showing is a plot showing the survival rate of medaka after treating with 1 µl of Peptide A (1.37 mM), Ampicillin (5.7 mM) or PBS followed by E. tarda injection after 2 hours (1 µl of E. tarda:$10^7$ CFU/ml). 20 fish per group. Log-rank (Mantel-Cox) test was applied for the comparison of survival curves (: p<0.01).

Peptide A is in particular capable of protecting Medaka from bacterial infection. The inventors injected E. tarda bacteria into medaka with or without Peptide A. As shown in FIG. 11B, medaka survival rate was significantly higher (80%) in fish co-injected with Peptide A and bacteria, compared with the ones without Peptide A treatment (35%). This result suggests that Peptide A can effectively inhibit E. tarda infection in fish. The inventors then tested whether medaka could be protected from bacteria-induced lethality by Peptide A. E. tarda was injected into the fish that had previously (2 h prior to bacteria injection) been injected with Peptide A. Control groups were either pre-injected with PBS or with Ampicillin. FIG. 11C shows that the initial survival rate (one day post injection) in Peptide A group (85%) was a little higher than the other two groups (about 45%). Interestingly, ampicillin appeared ineffective in treating E. tarda infection in medaka, two weeks after infection, and the number of surviving fish in the Peptide A group was still higher than the controls. Taken together, treatment of exogenous Peptide A appears to alleviate the effect of E. tarda infection on medaka.

DISCUSSION

The inventors observed that 301 of the SCPs are highly homologous with previously reported AMPs, with 74% homologous to antibacterial AMPs, consistent with the proportion of antibacterial peptides amongst the published AMPs. Interestingly, up to 20% of these peptides are homologous with AMPs previously discovered in amphibian skin secretions, including the Rugosin, Ascaphin and Gaegurin families. Cystatin, the largest family of AMPs identified so far, is not represented in the SCPs. This suggests that subsets of AMP classes with specific antimicrobial properties may be found in aquatic environments. The inventors further screened the remaining SCPs for possible antibacterial factors by using a prediction algorithm based on patterns and hidden Markov models generated from all the AMPs reported so far. After eliminating the non-amphipathic and anionic peptides from the predicted AMPs, the inventors shortlisted 430 peptides from the SCPs that are potential AMPs. The inventors experimentally tested the antibacterial activities of 53 of the 430 predicted peptides, and identified eight genuine AMPs. The relatively low hit rate suggests that current prediction algorithms for AMPs might not be applicable to short peptides. This inference is further supported by the observation that the truncation of Peptide A, one of the eight newly discovered AMPs, by one of the terminal amino acids could completely eliminate its antibacterial activity. These truncations do not significantly change the charge and hydrophobicity of Peptide A, and the shortened sequences were still predicted by all of the models in $CAMP_{R3}$ as potential AMPs. The data suggest that biochemical features which have not been considered by these AMP prediction models may contribute to the antimicrobial properties of these peptides, and these features might emerge with a more in-depth screening of the SCP library in future.

As the antibacterial effect of Peptide A depends on its sequence, it is believed that the action of this AMP may be mediated through sequence-specific binding to its intracellular targets, and not likely a result of the physical disruption of the charge and structure of the bacterial membrane. The proteomic analysis of the effect of Peptide A treatment on E. tarda revealed that some proteins related to the quality control of the outer membrane, such as peptidyl-prolyl cis-trans isomerase (SurA), peptidyl-prolyl cis-trans isomerase A (PpiA) and peptidyl-prolyl cis-trans isomerase B (PpiB), and FKBP-type peptidyl-prolyl cis-trans isomerase (FkpA), were extensively suppressed by Peptide A, thus suggesting that this AMP can suppress periplasmic protein folding. The proteome changes in Gram-negative bacteria treated with other AMPs have been studied, but the suppression of proteins involved in envelope stress responses have never been reported and appears to be a unique property of Peptide A.

Periplasmic proteins are highly sensitive to proteolysis and aggregation and therefore often require chaperone proteins to prevent proteolysis and aggregation. The suppression of SurA and other PPlases by Peptide A possibly leads to the accumulation of misfolded proteins in the periplasmic compartment. Interestingly, the inventors observed that trypsin-like serine protease (DegQ), a protein responsible for degrading misfolded proteins, was extensively increased in Peptide A treated cells, thus suggesting that unprotected outer membrane proteins (OMPs) are captured and degraded under Peptide A treatment. This will possibly lead to the depletion of OMPs and the disintegration of the outer membrane.

The envelope stress response is activated by two key regulators, the RpoE and CPX two component pathways. The proteomic results show that proteins involved in the CPX two component pathway, such as thiol:disulfide interchange proteins (DsbC), PpiA and FkpA, were down-regulated (FIG. 9A). The inventors then confirmed that the mRNA level of CpxR was significantly inhibited, while the other component, CpxA, was not changed after Peptide A treatment (FIG. 9B). However, CpxR and CpxA are adjacent genes encoded by the same CpxRA operon, suggesting that Peptide A effect on CpxR is post-transcriptional rather than at the level of gene transcription.

This result differs from the findings on ApoEdpL-W, an AMP derived from the human apolipoprotein E which can trigger the CpxAR stress pathways, possibly representing a general cellular response against AMPs. CpxR is known to activate the expression of efflux pump genes in P. aeruginosa and directly related to the development of resistance against both AMPs and antibiotics. The central role of CpxR in the survival mechanism of bacteria exposed to antimicrobials makes this gene an attractive drug target. For example, the depletion of the CpxR gene in bacteria increases sensitivity to antibiotics like β-lactams. As far as the inventors know, Peptide A is the first substance that can suppress the expression of CpxR, and is therefore an attractive lead compound as a CpxR inhibitor. In particular, Peptide A's ability to suppress the antibiotic induction of CpxR (FIG. 9C) makes it potentially suitable as a synergistic agent that can delay or even reverse antibiotic resistance. Furthermore, mutations of SurA, one of the CpxR regulons that was also suppressed by Peptide A, can increase the bacterial sensitivity to antibiotics due to defects in the membrane integrity.

The suitability of Peptide A as a potential antimicrobial therapeutic intervention is further supported by the observation that the D-isomer of this peptide is also functional as an AMP (FIG. 10), thus implying that a stable form of Peptide A can be manufactured. Indeed, the plasma origin of this peptide suggests that it is stable in body fluids. Furthermore, Peptide A is relatively nontoxic to mammalian cells (Table 3) at concentrations closed to its MIC. These cytotoxicity assays pave the way for future applications.

TABLE 3

Mammalian cell lines used

| Cell Line | Source | Organism | Tissue | Cell Type |
|---|---|---|---|---|
| HeLa | ATCC® CCL-2™ | Human | Cervix | Epithelial |
| MCF7 | ATCC® HTB-22™ | Human | Mammary Gland | Epithelial |
| MDA-MB | ATCC® CRM-HTB-26™ | Human | Mammary Gland | Epithelial |
| H1299 | ATCC® CRL-5803™ | Human | Lung | Epithelial |
| MC3T3 E1 | ATCC® CRL-2593™ | Mouse | Calvaria | Preosteblast |
| AG06858 | Coriell cell collection | Human | Foreskin | Fibroblast |

Peptide A is derived from vacuolar protein sorting-associated protein 13D-like (Vps13D), which belongs to none of the five general fish AMP classes (piscidins, β-defensins, hepcidins, cathelicidins and histone-derived AMPs). Hence, Peptide A appears to represent a class of conserved AMPs with a novel antibacterial mechanism. Vps13D is a member of the Vps13 family which was originally identified in yeast and is highly conserved among eukaryotes. While its function is largely unknown, a recent study reported that Vps13D can regulate interleukin-6 (IL-6) production in septic shock, which suggests that Vps13D may be involved in the human immune system. Peptide A as a unique AMP that suppresses the envelope stress response, an adaptive mechanism used by gram-negative organisms to negate antibiotics and AMPs, and is therefore a promising candidate in a new generation of antimicrobial agents. Peptide A may also be capable of synergizing the action of known AMPs and antibiotics, and stopping the emergence of antibiotic resistance.

EXPERIMENTAL PROCEDURES

Cells and Animals

The bacteria strains and mammalian cell lines used in this study are listed in Tables 2 and 3 respectively. All of the mammalian cells were cultured in low glucose Dulbecco's modified eagle medium (DMEM) (Invitrogen) supplemented with 10% (v/v) fetal bovine serum (Gibco), 1% (v/v) Antibiotic-Antimycotic (Invitrogen) and 1% (v/v) Glutamax (Invitrogen) in a humidified incubator supplied with 5% $CO_2$. The medium was changed every three days and the cells were subcultured when they reached 80% confluence. Japanese medaka (*Oryzias latipes*) were maintained at the City University of Hong Kong. The water temperature was maintained at 26° C.±0.5° C. and the light:dark cycle was adjusted to 14 h: 10 h. Water was replaced every two days with dechlorinated tap water. Fish were fed twice daily with lake food and once with *Artemia nauplii*.

Collection of Peptides from *O. latipes* Plasma

Plasma was collected from 32 healthy and bacterially infected medaka fish of both sexes and different ages (See Table 1 for details). Bacterial infection with *E. tarda* was performed as described in Ye, R. R. et al. *Environ. Sci. Pollut. Res.* (2016). Plasma from healthy and 3 day post infected fish was collected with syringes that contained a mixture of heparin (500 i.u/mL) and protease inhibitors (ROCHE complete protease Inhibitor Cocktail tablets) in phosphate buffered saline (PBS) after anesthetization of the fish with 0.04 mg/mL of ethyl-3-aminobenzoate methanesulfonate salt (MS-222; Sigma-Aldrich E10521, St. Louis, Mo.). To obtain small peptides, plasma were diluted in 25 mM ammonium bicarbonate (ABC) and 20% (v/v) acetonitrile (ACN) with 1:5 ratio to dissociate protein complexes in the plasma. After that, an Ultrafilter was used to fractionate peptides under 3 kDa in accordance with the manufacturer's instructions (Amicon® Pro Purification System with 3 kDa Amicon® Ultra-0.5 Device, ACS500302, Merck Millipore Ltd.). Filtrates were collected and concentrated by freeze-drying. The concentrated peptides were dissolved in 2% ACN with 0.1% TFA and then separated through high-performance liquid chromatography (HPLC; Dionex) on a C18 reverse phase column (inner diameter 75 µm, 5 µm of Acclaim PepMap100 medium; Dionex) over an 180 min gradient (mobile phase A: 0.1% fluoroacetic acid (FA) in 2% acetonitrile (ACN) in MilliQ water, mobile phase B: 0.1% FA in 98% ACN) and analyzed by a mass spectrometry MS/MS system (µTOFQII; Bruker Daltonics), as shown in FIG. 1. The resulting peak lists were generated by using Data Analysis, Version 4.0 (Bruker Daltonics). The MS data were searched against the NCBI database for *Oryzias latipes* (1411 release, 24,495 sequences searched), by using the MASCOT search engine (Matrix Science 2.3.02). The fixed modification was set as carbamidomethyl (C) and variable modification used was oxidation (M). No enzyme specificity was set and peptide charges of +2 and +3 were selected. Only ions with Mascot scores higher than 57 were taken into consideration. The identified fish circulating peptides were compared against the 2767 experimentally validated AMPs curated in $CAMP_{R3}$ by using BLASTP. A peptide was defined as highly homologous to a known AMP if the E-value of the BLASTP search was lower than 0.05, or if the amino acid sequences of the two peptides were at least 80% identical over 75% of the length of at least one of the sequences.

AMP Prediction

The antimicrobial activity of identified peptide sequences was predicted by interrogating the $CAMP_{R3}$ database[3] where each peptide was scored for likelihood of predicted antimicrobial property. Three algorithms provided by $CAMP_{R3}$ (http://www.camp.bicnirrh.res.in/), including Support Vector Machine (SVM), Random Forest (RF) and Discriminate Analysis (DA), were applied with probability values. At least one of probability values higher than 0.5 were regarded as novel AMPs. Furthermore, the physicochemical properties (length, molecular weight, net charge, pI and hydrophobic residues, GRAVY) of all identified sequences were calculated and the sequences were sorted by established AMPs properties. Length, charge and hydrophobic residues were calculated by using the APD2 database properties calculator. Molecular weight and pI were calculated using ENDMEMO (http://www.endmemo.com/bio/proie.php). The calculation of the grand average of hydropathy (GRAVY) was done by the following website: http://www.gravy-calculator.de/.

The identified fish circulating peptides were blast against around 2700 experimentally validated AMPs obtaining from $CAMP_{R3}$ by using BlastP provided by NCBI. The results either with identities higher than 80% (with coverage higher than 75%) or E values lower 0.05 are defined as highly homologous with known AMPs.

Peptide Synthesis

The peptides were synthesized through a conventional Fmoc-based solid-phase peptide synthesis in accordance with established protocols as described in Chen, G. et al. *ACS Appl. Mater. Interfaces* (2016). In brief, the peptides were synthesized on Rink amide resin. Fmoc-deprotection was carried out with 20% piperidine in dimethylformamide (DMF) while amino acid building blocks were coupled to the resin by using HOBT/HBTU/DIEA. C-terminal amidated peptide were synthesized as amide and capped in the amino terminal with acetic anhydride. The peptides were then cleaved with a mixture of TFA/TIPS/H$_2$O/EDT and characterized through MADI-TOF-MS (Bruker Daltonik GmbH, Bremen, Germany) as described in Chollet, B. et al. ACS Appl. Mater. Interfaces (2016). The peptides were purified by using a Shimadzu (Shimadzu Corporation, Japan) liquid chromatograph, equipped with a vacuum degasser, a binary pump, and a diode array detector (DAD) system, powered by Empower3 software. A reverse-phase Phenomenex Luna 5 µm C18 (2) 100 Å 50×3.0 mm column was used for separation at a column temperature of 30° C. The samples were separated by using a gradient of the mobile phase which contained Solvents A (acetonitrile) and B (0.1% trifluoroacetic acid (TFA) in water) with the following elution program: 0-3 min, 5-10% A; 3-15 min, 10-75% A; 15-18 min, 75-95% A; and 18-20 min, 95-5% A. The detection wavelengths were set at 215 nm and 254 nm. The flow rate was set at 5.0 ml/min and injection volume was 500 µL. The purified peptides (1.0 mg/mL) were dissolved in water or acetonitrile, and characterized by MALDI-TOF-MS (Bruker Daltonik GmbH, Bremen, Germany).

Circular Dichroism Spectroscopy

The secondary structure of the peptides was determined by using a circular dichroism (CD)-stopped-flow spectrophotometer (MOS-450 AFAF-CD). The samples were analyzed in a quartz cell with a path length of 1 cm, scanned from 180 to 250 nm at 25° C. with a scanning step of 0.125 nm and acquisition period of 0.05 s. The spectrum obtained was averaged over three consecutive scans and the solvent CD signal was subtracted. The potential secondary structure of the peptides was analyzed by using an online tool, BeStSel.

Antimicrobial Activities

Bacteria were grown in their respective media (Table 2 above) overnight at 37° C. or room temperature with constant shaking and then diluted to $10^6$ CFU/ml in their respective medium. Stock solutions of peptides at 0.68 mM were prepared in distilled water. Bacteria and peptide were incubated (50 µl: 50 µl) to make the final peptide concentrations (0.68, 3.4, 6.8, 13.7, 34.1, 68.3, 136.5 µM) in a 96-microtitre plate and incubated for 24 h with constant shaking. The control wells had the same amount of bacteria without the peptide. Absorbance at 600 nm was detected every 3 h up to 24 h to obtain the growth curves. The minimal inhibition concentration (MIC) was defined as the lowest concentration of an antimicrobial agent that could inhibit the growth of bacteria after overnight incubation.

Scanning Electron Microscopy

*E. tarda* and *S. pyogenes* cells ($10^6$ CFU/ml) were incubated with 34.1 µM of AMP or culture medium for 30 min, and then collected on a polycarbonate filter (pore size of 0.2 µm). The cells were fixed in 10% (v/v) glutaraldehyde diluted in PBS (pH 7.2) for 24 hrs at 4° C. The samples were viewed with a Philips XL30 ESEM FEG environmental scanning electron microscope (Philips Electronics, Netherlands, Europe) operated at 10 kV.

Proteomic Characterization of AMP-Treated Bacteria

Bacteria with or without AMP treatment for 1 hr at 6.8 µM were washed and lysed in 8 M of urea for 2 hrs. The lysate was then reduced in 10 mM of dithiothreitol (DTT) in 50 mM of ammonium bicarbonate (30 min at room temperature) and alkylated in 50 mM of iodoacetic acid (IAA) in 50 mM of ammonium bio-carbonate (20 min at room temperature). The samples were diluted 8 times with ammonium bicarbonate (50 mM, pH 8.0) so that the final concentration of urea was 1 M, followed by 2 µg of trypsin (Roche, Mannheim, Germany) for digestion. The mixtures were then incubated overnight at 37° C. and dried in a vacuum centrifuge (Eppendorf Concentrator plus). The peptides were dissolved in 20 µl of 0.1% trifluoroacetic acid (TFA), followed by ZipTip (Millipore, Billerica, Mass., USA) purification that was carried out in accordance with the manufacturer's instructions.

Mass spectrometry (MS) data were collected on an Orbitrap Fusion mass spectrometer coupled on-line with a nanoUPLC EASY-LC-1000 liquid chromatography system (ThermoFisher Scientific™, San Jose, Calif.). The peptides were eluted by using a microcapillary column with 50 cm×75 µm ID, PepMap C18, 2 µm particles (ThermoFisher Scientific™) with 2 to 80% acetonitrile in 0.1% formic acid at a flow rate of ~350 nL/min for 120 min of gradient. They were ionized through electrospray ionization (positive mode 2.1 kV), and survey scans of peptide precursors from 350 to 1550 m/z were performed at a resolution of 120 K at 200 m/z. Tandem MS was performed by isolation at 1.2 Th with the quadrupole component, fragmentation with normalized collision energy of 35%, and rapid scan MS analysis in the ion trap. The MS2 ion count target was set to 10E4 and the maximum injection time was 250 ms. Only precursors with a charge state of 2-7 were fragmented for the MS2 analysis. The dynamic exclusion duration was set to 60 s with a 10 ppm of low and high mass tolerance around the selected precursor and its isotopes. The instrument was run in data dependent mode by using Orbitrap and an ion trap with −3 s cycles.

The raw data were analyzed by using Proteome Discoverer (Version 1.4.0.288. Thermo Fisher Scientific). The MS/MS spectra were searched with the Mascot search engine against the NCBI bacteria database 2014 (with 29,574 sequence entries). The peptides were generated from a Lys-C and tryptic digestion and the precursor mass tolerance was set as 25 ppm, and 0.6 Da for fragment mass tolerances. The oxidation of methionine and deamidation of N, Q were set as the dynamic modification, and the carbamidomethylation of cysteine-C as the static modification. The peptide spectral matches (PSMs) were validated by using a percolator based on q-values at a 1% false discovery rate (FDR). For protein identification, a high-confidence database search with a peptide target FDR (strict) of 0.1%, and target FDR (relaxed) 0.5% and ranked 1 peptides were used for peptide filtering. Identified peptides were grouped into individual protein clusters by scaffolding.

Peptide quantitation was carried out by using Progenesis LC-MS (version 4.1, Nonlinear) and as described in Babaei, F. et al. *J. Proteome Res.* Eversion, (2013). In brief, the profile data of two sample groups with triplicates for each were converted into MS features. After "Automatic Alignment", all features with a charge that ranged from +2 to +7 were subjected to normalization. Following a statistical analysis, processing was carried out by using transformed "log-like" arcsin (ANOVA) calculations of all the detected features. The total cumulative abundance was calculated by summing the abundance of all peptides that belonged to a respective protein. The proteins were then ranked by p-value (one-way ANOVA) based on the sum of the normalized abundance across all runs.

Quantitative Real-Time PCR

E. tarda or E. coli were treated with AMP or antibiotics or not treated as the control at at inhibitory or subinhibitory for 1 hr. After that, the total RNA of the cells were collected by using the RNAprep pure cell/bacteria kit (TIANGEN), then reverse-transcribed into cDNA by using the One-Step FastQuant RT reagent kit with gDNase (TIANGEN). 18S ribosomal RNA (18S) was used as reference gene for qPCR normalization. Each group has 6 biological replicates. In brief, quantitative polymerase chain reaction (qPCR) assays were performed by using fluorescent dye powder SYBR Green PCR Master Mix and the ABI 7500 System. Gene-specific primers were designed with Primer-BLAST (NCBI). Specific primers were designed based on the sequence of the mRNA by the NCBI blast primer software. The primers used in the detection are listed in the Table 4 below. The relative expression levels (fold change) of the tested genes were calculated by using the relative expression based on the 2^(-Delta Delta C (T)) Method.

TABLE 4

Primers used in the detection.

| | Primer | | Sequence (5'-3') |
|---|---|---|---|
| E. tarda | CPXR | Forward | AGACGCCGGTCATTATGCTC (as shown as SEQ ID NO: 1) |
| | | Reverse | ACCAGCTCGCGATCATTGAA (as shown as SEQ ID NO: 2) |
| | CPXA | Forward | TACTGATGCTGCCCAAGCTC (as shown as SEQ ID NO: 3) |
| | | Reverse | GATCACCCGTCCTTCACTGG (as shown as SEQ ID NO: 4) |
| | RPOE | Forward | CCGGACAGTCCATGATAGCC (as shown as SEQ ID NO: 5) |
| | | Reverse | CGCACCATTGAGTCATTGCC (as shown as SEQ ID NO: 6) |
| | 16s | Forward | ACTGAGACACGGTCCAGACTCCTAC (as shown as SEQ ID NO: 7) |
| | | Reverse | TTAACGTTCACACCTTCCTCCCTAC (as shown as SEQ ID NO: 8) |
| E. coli | CPXR | Forward | AGGCGCTTGATCTTCTGGAC (as shown as SEQ ID NO: 9) |
| | | Reverse | GGAGATAGTCATCTGCGCCC (as shown as SEQ ID NO: 10) |
| | 16s | Forward | GTTAATACCTTTGCTCATTGA (as shown as SEQ ID NO: 11) |
| | | Reverse | ACCAGGGTATCTAATCCTGTT (as shown as SEQ ID NO: 12) |
| Meakada fish | VPS13D | Forward | GGAGGAAATCCCACCCCAAG (as shown as SEQ ID NO: 13) |
| | | Reverse | GGTTGCACTGTTTCGTCCAC (as shown as SEQ ID NO: 14) |
| | 18s | Forward | CCTGCGGCTTAATTTGACCC (as shown as SEQ ID NO: 15) |
| | | Reverse | GACAAATCGCTCCACCAACT (as shown as SEQ ID NO: 16) |

SOS Induction

E. coli PQ37 (Genotype: Sfi A and Lac Z fusion, lac Z) was cultured in lysogeny broth (LB) that contained 57.2 µM of ampicillin overnight (37° C.) and subcultured through 20 dilutions on another day so that OD600 equals to 0.2-0.4. PQ37 was incubated in 0.3 ml AMP (3.4 µM) or Piscidin (GWRTLLKKAEVKTVGKLALKHYL, 3.77 µM) for 2 hours and then re-suspended in the same volume of Z-buffer ($Na_2HPO_4 \cdot 7H_2O$ 16.1 g/l, $NaH_2PO_4 \cdot 2H_2O$ 6.24 g/L, KCl 0.75 g/L, $MgSO_4 \cdot 7H_2O$ 0.246 g/L and b-mercaptoethanol 0.3% (v/v)) for carrying out a β-galactosidase assay (β-ga) and alkaline phosphatase assay (ap), respectively. The bacteria were lysed with 0.1 ml of 0.1% SDS and 0.15 ml of chloroform. For the β-ga assay, the reaction was started by adding 0.6 ml of ortho-Nitrophenyl-β-galactoside (ONPG; Catalog number 34055, ThermoFisher Scientific) for color development and then stopped with the addition of 2 ml of 1 M $NaCO_3$ solution. For ap acsay, the reaction was started by adding 0.6 ml of para-Nitrophenylphosphate (PNPP; Catalog number 34045, ThermoFisher Scientific) for color development which was then terminated by the addition of 1 ml of 2 M HCl solution and 1 ml of 2 M Tri-HCl to restore the colour. The absorbance was read at 420 nm against a blank without bacteria. The induction factor (IF) was calculated as the ratio $R(x)/R(0)$ ($R(x)=\beta\text{-g}/ap$ determined for the tested peptide; $R(0)=\beta\text{-g}/ap$ determined for the LB). Furacin (antibiotic) and Piscidin were chosen as the controls. Each experiment was performed in triplicate.

In Vitro Toxicity Tests of AMP

Mammalian cell lines (Hela, MDA MB, MC3T3, MCF7, H1299, and AG06858) were seeded into 96 well-plates one day before treatment at a density of $3 \times 10^5$ cells/ml for a 48 hour MTT assay. The peptides were directly dissolved in the medium to make a 136.5 µM stock. After incubation with different cell lines in the 96-well plates for 48 hours, 5 mg/ml MTT stock in water was added into the 96 well-plates to yield a final concentration of 0.5 mg/ml in the culture medium. After 1 hr of incubation, the medium that contained the MTT was removed and replaced with dimethyl sulfoxide (DMSO) which dissolved the blue formazan product of the MTT with 30 minutes more incubation. The resulting solution was measured by using a microplate reader (BMG Polarstar Optima) at a wavelength of 570 nm. The optical density (OD) values were recorded and cell viability was calculated based on the OD readings normalized to the untreated cells.

In Vivo Effects of AMP on Bacterial Infection in Medaka Fish

The efficacy of the synthesized AMP to protect medaka against infection was characterized using host resistance assays with intraperitoneal (i.p.) injection of bacteria using a micro-injection machine (PV820 Pneumatic PicoPump). In Experiment One, 80 medaka fish were used and divided into four groups (20 fish in each group, male, 6 months): (1) Group 1 was injected with only 1 µl of PBS in each fish; (2) Group 2 was injected with only 1 µl of novel AMP (0.68 mM) in each fish; (3) Group 3 was injected with 1 µl of bacteria (at a titer of $5 \times 10^7$ CFU/ml); and (4) bacteria and novel AMP were mixed for 5 min and then 1 µl of the mixture was injected into Group 4 (Bacteria: $5 \times 10^7$ CFU/ml, AMP: 0.68 mM). In Experiment Two, 60 fish were used and divided into three groups: each fish was injected with 1 µl of PBS, ampicillin (5.7 mM) or Peptide A (1.36 mM). The fish were anesthetized in MS222 for 30 s before microinjection. After two hours, 1 µl of bacteria ($5 \times 10^7$ CFU/ml) was injected into the fish. All of the fishes were kept under a static condition of 26° C.±1° C., with 14:10 hrs of a light-dark cycle. The water was replaced every two days. The fish were fed three times each day. The number of dead fish was counted on a daily basis until two weeks after the injections.

Statistical Data Analysis

Data were displayed as mean±SD. For statistical test, either the T test (two samples comparison) or ANOVA (multiple group comparisons) was applied in the study. Excel 2007 and GraphPad Prism 6 were used to perform statistical analysis. When two-way ANOVA was applied, Dunnett's multiple comparisons test was performed as well. Log-rank (Mantel-Cox) test was applied for the comparison of survival curves in fish efficacy study. An alpha value $p<0.05$ (*) or $p<0.01$ (**) was considered statistically significant.

The invention claimed is:

1. A pharmaceutical composition for treating a bacterial infection, comprising an effective amount of a peptide and a pharmaceutically tolerable excipient, wherein the peptide consists of the amino acid sequence of SEQ ID NO: 17.

2. The pharmaceutical composition of claim 1, wherein the peptide has a concentration of about 0.1 μM to about 150 μM.

3. An analog of a peptide comprising the amino acid sequence of SEQ ID NO: 17,
   wherein one or more amino acids residues of the amino acid sequence are modified by
   a) C-terminal modification;
   b) D-amino acid substitution; and/or
   c) deletion of one amino acid residue at C- or N-terminus.

4. The analog of claim 3, wherein the analog has a net charge of at least 5.

5. The analog of claim 3, wherein the analog is a C-terminal amidated peptide.

6. The analog of claim 3, wherein the analog consists of D-amino acids.

7. A method of treating a bacterial infection in a subject, comprising administering an effective amount of a peptide to the subject, wherein the peptide comprises the amino acid sequence of SEQ ID NO: 17.

8. The method of claim 7, wherein the bacterial infection is an antibiotic-resistant bacterial infection.

9. The method of claim 7, wherein the subject is a mammal.

10. The method of claim 7, wherein the subject is a fish.

11. The method of claim 7, wherein the subject is administered with the peptide at a concentration of about 0.1 μM to about 150 μM.

12. The method of claim 7, wherein the bacterial infection is caused by a gram-negative bacterium selected from *A. hydrophila, V. alginolyticus, E. coli, E. tarda, A. baumannii* or a combination thereof.

13. The method of claim 7, wherein the bacterial infection is caused by a gram-positive bacterium selected from *S. faecalis, S. pyogenes, S. Aureus*, or a combination thereof.

* * * * *

SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Synthesized

<400> SEQUENCE: 1
agacgccggt cattatgctc                                        20

<210> SEQ ID NO 2
<211> LENGTH: 20
<212> TYPE: DNA
<213> ORGANISM: Artificial Sequence
<220> FEATURE:
<223> OTHER INFORMATION: Synthesized

<400> SEQUENCE: 2
accagctcgc gatcattgaa                                        20

<210> SEQ ID NO 3
<211> LENGTH: 20
<212> TYPE: DNA
<213> ORGANISM: Artificial Sequence
<220> FEATURE:
<223> OTHER INFORMATION: Synthesized

<400> SEQUENCE: 3
tactgatgct gcccaagctc                                        20

<210> SEQ ID NO 4
<211> LENGTH: 20
<212> TYPE: DNA
<213> ORGANISM: Artificial Sequence
<220> FEATURE:
<223> OTHER INFORMATION: Synthesized

<400> SEQUENCE: 4
gatcacccgt ccttcactgg                                        20

<210> SEQ ID NO 5
<211> LENGTH: 20
<212> TYPE: DNA
<213> ORGANISM: Artificial Sequence
<220> FEATURE:
<223> OTHER INFORMATION: Synthesized

<400> SEQUENCE: 5
ccggacagtc catgatagcc                                        20

<210> SEQ ID NO 6
<211> LENGTH: 20
<212> TYPE: DNA
<213> ORGANISM: Artificial Sequence
<220> FEATURE:
<223> OTHER INFORMATION: Synthesized

<400> SEQUENCE: 6
cgcaccattg agtcattgcc                                        20

<210> SEQ ID NO 7
<211> LENGTH: 25
<212> TYPE: DNA
<213> ORGANISM: Artificial Sequence

```
<220> FEATURE:
<223> OTHER INFORMATION: Synthesized

<400> SEQUENCE: 7
actgagacac ggtccagact cctac                                              25

<210> SEQ ID NO 8
<211> LENGTH: 25
<212> TYPE: DNA
<213> ORGANISM: Artificial Sequence
<220> FEATURE:
<223> OTHER INFORMATION: Synthesized

<400> SEQUENCE: 8
ttaacgttca caccttcctc cctac                                              25

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
aggcgcttga tcttctggac                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthesized

<400> SEQUENCE: 10
ggagatagtc atctgcgccc                                                    20

<210> SEQ ID NO 11
<211> LENGTH: 21
<212> TYPE: DNA
<213> ORGANISM: Artificial Sequence
<220> FEATURE:
<223> OTHER INFORMATION: Synthesized

<400> SEQUENCE: 11
gttaataccT ttgctcattg a                                                  21

<210> SEQ ID NO 12
<211> LENGTH: 21
<212> TYPE: DNA
<213> ORGANISM: Artificial Sequence
<220> FEATURE:
<223> OTHER INFORMATION: Synthesized

<400> SEQUENCE: 12
accagggtat ctaatcctgt t                                                  21

<210> SEQ ID NO 13
<211> LENGTH: 20
<212> TYPE: DNA
<213> ORGANISM: Artificial Sequence
<220> FEATURE:
<223> OTHER INFORMATION: Synthesized

<400> SEQUENCE: 13
ggaggaaatc ccaccccaag                                                    20
```

```
<210> SEQ ID NO 14
<211> LENGTH: 20
<212> TYPE: DNA
<213> ORGANISM: Artificial Sequence
<220> FEATURE:
<223> OTHER INFORMATION: Synthesized

<400> SEQUENCE: 14
ggttgcactg tttcgtccac                                              20

<210> SEQ ID NO 15
<211> LENGTH: 20
<212> TYPE: DNA
<213> ORGANISM: Artificial Sequence
<220> FEATURE:
<223> OTHER INFORMATION: Synthesized

<400> SEQUENCE: 15
cctgcggctt aatttgaccc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthesized

<400> SEQUENCE: 16
gacaaatcgc tccaccaact                                              20

<210> SEQ ID NO 17
<211> LENGTH: 13
<212> TYPE: PRT
<213> ORGANISM: Oryzias latipes

<400> SEQUENCE: 17

Ile Arg Ile Ile Leu Arg Ala Gln Gly Ala Leu Lys Ile
1               5                   10
```